United States Patent [19] [11] 4,105,856
Newton [45] Aug. 8, 1978

[54] RECOVERY PROCESS FOR AQUEOUS WASTE STREAMS IN ADIPIC ACID SYSTEMS

[75] Inventor: Cecil A. Newton, Odessa, Tex.

[73] Assignee: El Paso Products Company, Odessa, Tex.

[21] Appl. No.: 76,624

[22] Filed: Sep. 29, 1970

[51] Int. Cl.$^2$ .................. C07C 69/34; C07C/67/48; C07C 69/42; C07C 69/44

[52] U.S. Cl. ............................ 560/191; 560/204;

[58] Field of Search .................. 260/485; 560/204

[56] References Cited

U.S. PATENT DOCUMENTS 2,824,122   2/1958   Kuceski .................... 260/485

FOREIGN PATENT DOCUMENTS 933,714   8/1963   United Kingdom .................... 260/485

OTHER PUBLICATIONS

C & E News, p. 50, Jul. 20, 1970.

Primary Examiner—Jane S. Myers
Attorney, Agent, or Firm—Depaoli & O'Brien

[57] ABSTRACT

By-product or waste streams from adipic acid plants which contain adipic acid, glutaric acid, succinic acid, nitric acid and catalyst values of copper and vanadium are treated to substantially recover all the components thereof by esterifying the dibasic acids with an alcohol, such as normal butanol, which creates esters that are substantially immiscible in the aqueous solution, allowing the organic esters to form a separate layer from the aqueous phase in which the metal values are retained, recovering the organic layer containing the esterified dibasic acids and thereafter re-using the aqueous solution containing the catalyst values in the adipic acid process.

4 Claims, No Drawings

RECOVERY PROCESS FOR AQUEOUS WASTE STREAMS IN ADIPIC ACID SYSTEMS

CROSS REFERENCES TO RELATED APPLICATIONS

This application is related to copending Application Ser. Nos. 766,476, now U.S. Pat. No. 4,076,948, 851,445, now U.S. Pat. No. 4,082,788, and 843,028, now U.S. Pat. No. 4,058,555, of S. Mims of the same assignee.

BACKGROUND OF THE INVENTION

1. Field of the Invention

This invention relates to a process for the recovery of organic acids and other useful products such as nitric acid and catalyst values contained in aqueous nitric acid solutions resulting from the oxidation of cyclohexanol and/or cyclohexanone to produce adipic acid.

2. Description of the Prior Art

The art is well aware of processes for producing useful acids, such as adipic acid, by oxidizing naphthenes, cycloaliphatic ketones or cycloaliphatic alcohols with nitric acid in the presence of metal compound oxidation catalysts. Such processes in general involve heating specific cyclic ketones and/or alcohols such as cyclohexane, cyclohexanol and/or cyclohexanone in nitric acid at about 40° to 140° C., generally utilizing nitric acid of about 20 to 90 percent strength, to produce a resulting oxidation mixture comprising the adipic acid together with small amounts of other dicarboxylic acids in admixture with the unused nitric acid and catalyst components. Generally, the art subsequently recovers a substantial amount of the desirable product, adipic acid, by cooling the solution and filtering off the crystallized adipic acid. Such processes for producing adipic acid in this manner are known in the prior art, for examples from U.S. Pat. Nos. 2,791,566; 2,840,607; 3,338,959; 2,971,010; 2,439,513; and 2,557,282.

Adipic acid, of course, is an important intermediate for the production of nylon by subsequent copolymerization with hexamethylenediamine to produce a polyamide capable of being spun into a fiber having a number of desirable characteristics.

In the processes known to the art, however, very little attention has been paid to recovery of the valuable materials which can be further utilized by recycling the same to the nitric acid oxidation process such as unused nitric acid and catalytic components. Moreover, the adipic and other organic acids contained therein have usually been treated as waste materials.

In the process for nitric acid oxidation of cyclohexanol and/or cyclohexanone, significant amounts of succinic acid and glutaric acid are formed as by-products in admixture with the adipic acid. Various well known schemes of crystallization, concentration and further crystallization have been used heretofore in industry to attempt separation thereof and usually a substantial amount of the adipic acid can be removed by these procedures. Ultimately, however, a mother liquor is obtained from these operations which contains succinic acid, glutaric acid, and a small amount of adipic acid in such proportions that further concentration and crystallization steps will yield only mixtures of these dibasic acids. In addition, as a result of the removal of the adipic acid by crystallization and removal of the water and nitric acid by volatilization, the concentration of the metal catalyst in this final mother liquor becomes relatively high. Hence, loss of these materials, particularly the catalytic components, provides a distinct economic disadvantage as the relatively high proportion of valuable and reusable products is lost.

As pointed out above, this waste stream has heretofore been merely dumped into the sewer and because of the corrosive materials present, contributed substantially to the pollution of rivers and streams. The process of the present invention provides a processing technique which prevents further pollution from this waste stream in production of one of our most valuable products.

It is clear, therefore, that a distinct need remains in the art for processes by which this nitric acid oxidation mother liquor may be processed so as to recover the valuable components contained therein in an economic and efficient manner and prevent the pollutive effects formerly involved in processing this waste stream.

SUMMARY OF THE INVENTION

It is accordingly one object of the present invention to provide a process for the removal and recovery of organic dibasic acids and the other valuable components contained in nitric acid-containing mother liquors from adipic acid production systems.

A further object of the invention is to provide a method for the recovery of such materials in re-useable form uncontaminated by the presence of the other materials.

A still further object of the invention is to provide an esterification process by which these materials may be recovered without the addition thereto of materials which would tend to accumulate in re-cycle streams and eliminate costly recrystallization and filtration steps.

An even further object of the invention is to provide a method for the treatment of waste streams from commercial adipic acid plants by an esterification/separation technique by which the corrosive materials contained in the adipic acid stream are recovered and re-used so as to thereby prevent pollution of rivers and streams.

Other objects and advantages of the present invention would become apparent as the invention proceeds.

In satisfaction of the foregoing objects and advantages, the process of the present invention provides a procedure for the removal and recovery of organic acids, either in the form of their esters or as the free acid form, and the recovery of metal catalytic values and nitric acid components contained in the dilute aqueous nitric acid stream resulting from the nitric acid oxidation of cyclohexanol and/or cyclohexanone in the presence of metal compound oxidation catalysts such as copper and vanadium. The invention comprises a process for separating dibasic acids from a nitric acid oxidation reaction mixture containing the catalyst values by esterifying the dibasic acids by the addition of an alcohol, such as normal butanol, so as to create esters that are immiscible in the aqueous mother liquor, allowing the organic esters to form a separate layer from the aqueous phase, the copper and vanadium catalyst being retained in the aqueous phase, and thereafter separating layers and re-using the aqueous solution containing the catalyst in the nitric acid oxidation reaction.

Also within the scope of this invention are procedures whereby the aqueous phase may be processed to recover the nitric acid and metal catalyst values contained therein for re-cycle to the adipic acid manufacturing system, processes for recovery of the diesters of succinic acid, glutaric acid and adipic acid as well as procedures for hydrolysis of these esters back to the original acids and recovery thereof.

DESCRIPTION OF PREFERRED EMBODIMENTS

As pointed out above, the process of this invention provides a procedure for the removal and recovery of valuable organic acids, either in the form of their esters or the acids per se, nitric acid and catalytic components contained in the mother liquor resulting from the nitric acid oxidation of cyclohexanol and/or cyclohexanone in the presence of metal compound oxidation catalysts to produce essentially adipic acid. The process also provides means whereby the metal oxidation catalysts and the nitric acid contained therein can be recovered in a form suitable for re-cycle to the original oxidation process.

The waste stream from an adipic acid plant, after removal of as much of the adipic acid as possible, includes a substantial amount of unspent nitric acid, a difficultly separable mixture of dibasic acids including some adipic acid, succinic acid and glutaric acid, copper and vanadium or other metal catalyst values. To the present, this mixture has been generally unuseable because of the difficulty in separation and recovery of the components contained therein. Accordingly, it has previously been the practice in adipic acid plant operations to consider this stream as a waste stream. This mother liquor will generally be found to contain the following components in the percent indicated based on the total weight of the mother liquor.

| Component | Amount |
|---|---|
| Succinic acid | 3–10% |
| Glutaric acid | 8–35% |
| Adipic acid | 3–6% |
| Nitric acid | 6–20% |
| Catalyst | 1–3% |
| Water | Balance |

Thus, this adipic acid waste stream or mother liquor, in a commercial scale operation, will be seen to contain a substantial amount of materials which are sufficiently valuable to be recovered to render the original oxidation process efficient and economical. This will also overcome a significant pollution problem as explained above.

According to this invention, it has been found that these valuable components can be separated and/or recovered by adding to the stream a suitable alcohol, for example, normalbutyl alcohol, under such conditions that the alcohol forms esters with the organic acids present in the stream. These esters, together with most of the unreacted organic components of the stream, are substantially immiscible with and separate from the aqueous stream as an immiscible layer. Hence the formation of an organic layer or phase and an aqueous layer or phase will be observed. When the concentration of dibasic acids has been reduced to a desired level, the remaining aqueous phase, containing the copper and vanadium or other metal catalyst values and nitric acids may be concentrated by distillation which also removes any alcohol not extracted into the organic phase. This concentrated aqueous phase containing some nitric acid, copper and vanadium may then be returned to the adipic acid plant in a re-cycle operation.

The separated organic phase may be water-washed to recover most of the nitric acid contained therein. In one embodiment, the washed organic phase may then be distilled to recover the individual esters, i.e., the diesters of glutaric acid, adipic acid and succinic acid. An important aspect of the invention is that the diesters of each of these acids have sufficiently different boiling points so that they can be suitably separated by fractional distillation. On the other hand, separation of the acids per se, by distillation is impractical which is the reason that the original filtrate is not suitable for diacid recovery by distillation. Therefore, the process provides a system for recovery of dibasic acids in the form of their diester derivatives.

On the other hand, the washed organic phase still contains sufficient nitric acid to serve as a catalyst for hydrolysis purposes. Thus, if the organic phase is distilled in the presence of water to hydrolyze the esters, the alcohol may be recovered for reuse leaving a mixture of acids as a residue. The alcohol recovered may then be recycled in a continuous process.

If the hydrolysis reaction is carried out, the distillation bottoms will consist of regenerated dibasic acids in an aqueous solution with adipic acid being the least soluble component of the solution. By varying the temperature, i.e. cooling, and/or concentration of this solution, a further portion of adipic acid can be precipitated for recovery leaving the succinic acid and glutaric acid.

The alcohol chosen for the esterification step is one which boils lower than water or forms a minimum-boiling azeotrope with water. Normal-butyl alcohol has been found to be particularly desirable as an esterification alcohol as it eminently satisfies all necessary criteria. If the alcohol chosen is only partially immiscible with water, as is normal-butyl alcohol, then the overhead product on distillation will separate into an alcohol and a water layer by which the water can be continuously returned to the pot to promote hydrolysis of esters and aid in removing the alcohol if that embodiment is used. The alcohols which may in general be used are those straight and branched chain higher alcohols of the formula R-OH, wherein R is alkyl of 4 to about 20 carbon atoms. Illustrative of such alcohols are n-butyl alcohol, sec.-butyl alcohol, amyl alcohol, tert.-amyl alcohol, sec.-isoamyl alcohol, 2,3,3-trimethyl-2-butanol, isoamyl alcohol, 2-hexanol, 2-methyl-2-hexanol, 5-methyl-2-hexanol, 3-hexanol, and the like. Mixtures of alcohols may also be employed.

The selection of the alcohol to use in the esterification is therefore based on the following criteria:

(1) Its resistance to nitric acid oxidation during the extraction step;

(2) its solubility characteristics;

(3) the ease of formation and hydrolysis of the esters it forms;

(4) its volatility, azeotropic properties and other distillation characteristics: and (5) its price and availability, this latter being particularly necessary for use in a commercial operation.

The esterification reaction may be carried out at any desired temperature but a preferred range is from room temperature up to about the boiling point of the alcohol used. A preferred temperature is about 50° to 75° C.

After the addition of alcohol to the solution, it will be observed that two layers are formed as the esterification proceeds. The nitric acid present in the adipic acid stream provides the necessary catalytic agent for the esterification. After the esterification is complete, the organic phase and the aqueous phase are separated. The organic phase is then processed as discussed hereinabove. The aqueous phase is most suitably processed by subjecting to distillation to remove any alcohol and water fractions and thereafter re-cycling the remaining residue containing nitric acid concentrated in the catalytic components, copper and vanadium, to the nitric acid oxidation process.

This latter aspect constitutes a very important portion of the process of this invention in that it enables the provision of a continuous recovery and re-cycle system in processing of adipic acid waste streams. Thus, in this procedure, the waste stream can be continuously esterified by the addition of an alcohol such as normal-butyl alcohol thereto with continuous separation of layers as they are formed in a separation tank. Thereafter, the organic phase can be processed for recovery of the esters and/or the alcohols and the hydrolyzed acids, whereas the aqueous stream can be subjected to distillation for recovery of excess alcohol and water and the remaining residue can be recycled to the nitric acid oxidation process for further adipic acid production.

The ester mixture resulting from the organic phase is in itself valuable to prepare high molecular weight esters useful as plasticizers or resins such as polyvinyl chlorides. However, the esters may be further fractionated to yield in pure form the diester of succinic acid, diester of glutaric acid and the diester of adipic acid. Thereafter, these individual ester compounds can be hydrolyzed either separately or in a mixture to yield a pure acid or can be processed in other ways to yield useful products.

As pointed out above, the process has been generally described with respect to operation by the batch method. However, the process is admirably suited to be conducted in a continuous manner by the method outlined above.

The theory of the process of the present invention is based on the fact that the esters formed from the dibasic acids in the mixture have solubility characteristics typical of non-polar compounds and will not remain in solution in the aqueous filtrate to more than a neglible extent. Esterification reactions of this type are known to be equilibrium situations according to the following equation:

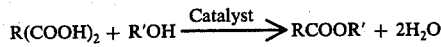

$$R(COOH)_2 + R'OH \xrightarrow{Catalyst} RCOOR' + 2H_2O$$

If a component on one side of the equation is continuously removed from the system, then the system reacts to restore the balance of that component in the system. Since the removal is continuous, balance is never actually restored and thus the reaction is driven to completion. It is to be observed that the action of the esters in splitting out of the aqueous phase in the present process constitutes such a continuous removal. Of course, the ester phase will split out of the filtrate only to the extent that the amount of ester formed exceeds solubility of the ester in the aqueous phase. A small amount of ester will probably always remains in the aqueous phase, thus, setting some limit on the extent to which the esterification can proceed. Even with this limitation, however, the reaction proceeds far enough to achieve a high degree of removal.

In the esterification step, as the esters separate from the aqueous phase, they will extract some of the unreacted alcohol, retarding the reaction. The ratio of alcohol in the aqueous phase or organic phase will depend on the distribution coefficient for the system. As the alcohol in the aqueous phase reacts, the aqueous phase will become depleted in alcohol and more alcohol dissolves in the organic phase to restore the balance required by the distribution coefficient. On the other hand, the newly formed esters from the reaction will go to increase the amount of organic phase and hence this capacity to dissolve more alcohol. These two forces tend to produce opposite effects and they cancel each other out. For completeness of dibasic acid removal it is essential that a fair amount of alcohol remain the aqueous phase after the esters start to separate. On the other hand if too much alcohol remains it will tend to hold esters in the aqueous phase. The alcohol used in excess may then of course be recovered during the processing steps.

As opposed to prior art techniques, the present process is simple and economical but still affords the simultaneous recovery of dibasic acids as well as of the metallic catalysts contained in the mixture. Moreover, the materials are recovered in highly useful form, the dibasic acids being recovered as diester derivatives useful as a mixture or easily processed by further means to yield individual compounds such as the individual esters, by hydrolysis to recover the acids; by transesterification to produce more useful, particularly high molecular weight, esters. The metal catalysts are recovered as a concentrated solution in nitric acid and thus, in an ideal form for reuse in the cyclohexanol/cyclohexanone nitric acid oxidation reaction.

The following examples further exemplify certain embodiments of the process but the invention is not to be considered as limited thereto.

In these examples, parts are by weight unless otherwise indicated.

EXAMPLE I

A final aqueous adipic acid mother liquor filtrate containing 18.4 wt.% nitric acid and 19.3 wt.% of a mixture of organic acids calculated as adipic acid was used as the solution to be extracted and n-butyl alcohol was the esterifying alcohol. The normal-butyl alcohol was added to the system and on esterification by heating at 70° C., an organic phase separated. After layer separation, analysis of the aqueous phase indicated that it contained 17.7 wt.% nitric acid and 9.2 wt.% organic dibasic acids calculated as adipic acid. Thus, the n-butyl alcohol in fact esterified and extracted about one-half of the dibasic acids present in the solution.

EXAMPLE II 101.3 grams of an adipic acid filtrate containing 18.4 wt.% nitric acid, 19.3 wt.% dibasic organic acids calculated as adipic acid and catalyst values of copper and vanadium, and 40.1 grams of normal-butyl alcohol were heated on a hot plate with stirring to 50° C., held there approximately 10 minutes, and cooled to room temperature. The organic phase and an aqueous phase were left in a separatory funnel approximately one hour to allow good separation of the phases. On separation of layers, the aqueous phase recovered was 75.1 grams, and the organic phase recovered was 64.7 grams, thereby resulting in a 1.6 gram loss.

The aqueous phase was then washed with 10.1 grams of cyclohexane, 6.2 grams of water was added by mistake resulting in a recovery of 78.2 grams of the aqueous phase.

The organic phase was washed with 9.9 grams of distilled water to result in a recovery of 57.4 grams of an organic phase.

Analysis of the aqueous phase before the washing step showed 17.0 wt.% nitric acid, and 2.9 wt.% organic acids calculated as adipic acid thus indicating that most of the organic acids had been removed. The organic phase before washing analyzed 7.3 wt.% nitric acid and 4.0 wt.% organic acids as adipic acid. After the washing step the organic phase analyzed 14.6 wt.% nitric acid and 1.2 wt.% organic acids calculated as adipic acid. The aqueous phase after wash analyzed 0.7 wt.% nitric acid and 0.5 wt.% organic acids calculated as adipic acid.

EXAMPLE III

The aqueous phase from Example II was then subjected to distillation under vacuum at 120 mm. Hg. The $HNO_3$ concentration in overhead cuts or fractions progressed smoothly from 41.4% in the first cut to 78.1% in the seventh cut. The pot temperature went from 79.5° to 122° C. and the overhead temperature from 72.5° to 77.5° C. in same interval. Solids appeared in pot when temperature passed 100° C. Dense brown fumes indicated $HNO_3$ decomposition at a temperature of about 115°–122° C. (Pot temperature was climbing rapidly at this point). At this point 70 cc water were added initially and more gradually as needed to control pot temperature and distillation continued. $HNO_3$ in fractions then went from 16.0% in the eighth cut to 2.4% in the eleventh cut. Pot temperature was controlled at about 120° C. On completion of the distillation and cooling, the pot contents become solid. From this distillation 76.1% of $HNO_3$ was recovered.

EXAMPLE IV 49.3 Grams of the butyl ester phase from the esterification experiment of Example II was charged to a 100 ml. flask along with 39.7 grams of water to aid the hydrolysis of the esters present.

The following is an analysis of the charge to the flask:

| Product | Wt. % | Grams | Butanol Recoverable Grams |
|---|---|---|---|
| Butanol | 65.4 | 32.3 | 32.3 |
| Light Fraction (Unknown) | 2.3 | 1.1 | — |
| Oxalic Acid Ester | 0.1 | 0.1 | 0.1 |
| Succinic Acid Ester | 3.1 | 1.5 | 1.0 |
| Glutaric Acid Ester | 12.4 | 6.1 | 3.7 |
| Adipic Acid Ester | 5.4 | 2.7 | 1.5 |
| Heavy Fraction (Unknown) | 4.0 | 2.0 | — |
| Nitric Acid | 7.3 | 3.6 | — |
| Total | 100.0 | 49.3 | 38.5 |

This mixture was then subjected to distillation together with the 39.7 grams of water added. During the distillation the overhead temperature varied from 60° C. in the early stages up to 102° C. in the later stages, all at atmospheric pressure. Most of the take-off was between 75° and 90° C. $HNO_3$ decomposition was observed by the presence of brown fumes when the overhead temperature reached 102° C. The apparatus had no provision for continuous return of the aqueous phase to the flask so the system was operated by distilling off n-butanol and water until the overhead temperature reached 100° C., shutting the system down, cooling, and returning the aqueous phase to the pot. Operating in this manner, there was a total recovery of 83.5 grams (a 5.5 gram loss) of which 35.6 grams was OH-organic phase, 25.6 grams was OH-aqueous phase, and 22.3 grams was the pot residue. Analysis of the organic phase and aqueous phase showed the presence of 34.7 grams n-butanol (a theoretical recovery of 90.6%). In the organic phase there was 0.2% light unknown, 0.1% oxalic ester, 0.2% succinic ester, 0.3% glutaric ester, 0.1% adipic ester and 0.1% heavy unknown. Hence the deesterification was substantially complete.

The invention has been described hereinabove with reference to certain preferred embodiments. However, it is to be understood that the invention is not to be limited thereto as obvious modification thereon will be apparent to those skilled in the art.

What is claimed is:

1. In a process for the treatment of the mother liquor resulting from the nitric acid oxidation of cyclohexanol and/or cyclohexanone and the recovery of valuable components therefrom, which mother liquor is a mixture comprising from about 3 to 10 weight percent succinic acid, from about 8 to 35 weight percent glutaric acid, from about 3 to 6 weight percent adipic acid, from about 6 to 20 weight percent nitric acid, and from about 1 to 3 weight percent vanadium and copper metal catalyst values, the improved process which comprises:
   (a) contacting said mother liquor with an organic alcohol of the formula ROH wherein R is an alkyl of 4 to about 20 carbon atoms which will create esters which are substantially immiscible with the resulting aqueous solution and in a sufficient amount to esterify at least a portion of the aliphatic dibasic acids present, said contact being at a temperature ranging from room temperature up to about the boiling point of the alcohol employed;
   (b) allowing the organic esters to form a separate organic phase from an aqueous phase;
   (c) separating said organic phase from said aqueous phase;
   (d) distilling said organic phase to recover the esters of the dibasic acids therefrom, and
   (e) concentrating the aqueous phase to recover a concentrated nitric acid solution containing the metallic catalyst values.

2. A process according to claim 1 wherein the esterification reaction is conducted at a temperature from about 50° to 75° C.

3. A process according to claim 2 wherein the organic phase is distilled in the presence of added water to hydrolyze the diesters during distillation to recover the adipic acid, glutaric acid and succinic acid therefrom.

4. A process according to claim 2 wherein the alcohol is n-butyl alcohol.

* * * * *